United States Patent
Bhagavatula et al.

(10) Patent No.: US 10,162,114 B2
(45) Date of Patent: Dec. 25, 2018

(54) REFLECTIVE OPTICAL COHERENCE TOMOGRAPHY PROBE

(71) Applicant: Corning Incorporated, Corning, NY (US)

(72) Inventors: Venkata Adiseshaiah Bhagavatula, Big Flats, NY (US); Klaus Hartkorn, Big Flats, NY (US); Daniel Max Staloff, Rochester, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/989,261

(22) Filed: Jan. 6, 2016

(65) Prior Publication Data

US 2016/0202417 A1     Jul. 14, 2016

Related U.S. Application Data

(60) Provisional application No. 62/101,105, filed on Jan. 8, 2015.

(51) Int. Cl.
  *G02B 6/26* (2006.01)
  *G02B 6/36* (2006.01)
  *G01B 9/02* (2006.01)
  *A61B 5/00* (2006.01)

(52) U.S. Cl.
  CPC ............ *G02B 6/262* (2013.01); *A61B 5/0084* (2013.01); *A61B 5/6852* (2013.01); *G01B 9/0205* (2013.01); *G01B 9/02038* (2013.01); *G01B 9/02091* (2013.01); *G02B 6/3636* (2013.01)

(58) Field of Classification Search
  CPC .. G02B 6/262; G02B 6/3636; G01B 9/02038; G01B 9/02091; G01B 9/0205; A61B 5/0084; A61B 5/6852
  See application file for complete search history.

(56) References Cited

U.S. PATENT DOCUMENTS

| | | | |
|---|---|---|---|
| 6,904,197 B2 | 6/2005 | Bhagavatula et al. | |
| 8,675,293 B2 * | 3/2014 | Flanders | B29D 11/0073 359/621 |
| 2005/0201662 A1 | 9/2005 | Petersen et al. | |
| 2006/0067620 A1 | 3/2006 | Shishkov et al. | |
| 2009/0323076 A1 | 12/2009 | Li et al. | |
| 2010/0253949 A1 | 10/2010 | Adler et al. | |
| 2013/0266259 A1 * | 10/2013 | Bhagavatula | G02B 6/32 385/33 |

(Continued)

OTHER PUBLICATIONS

PCT International Searching Authority; International Search Report and Written Opinion; Application No. PCT/US2016/012558; International Filing Date Jan. 8, 2016; dated Apr. 7, 2016; pp. 1-12.

(Continued)

*Primary Examiner* — John M Bedtelyon
(74) *Attorney, Agent, or Firm* — Svetlana Z. Short

(57) ABSTRACT

A beam-shaping optical system suitable for use with optical coherence tomography includes a beam-shaping body having a beam-shaping element and an alignment feature. An optical fiber is coupled to the alignment feature. The fiber has a fiber end configured to emit an electromagnetic beam. The fiber and the body are configured to direct the beam into the beam-shaping element such that the beam is shaped solely by reflection into an image spot.

17 Claims, 4 Drawing Sheets

(56) References Cited

U.S. PATENT DOCUMENTS

| | | | |
|---|---|---|---|
| 2013/0305513 A1 | 11/2013 | Flanders et al. | |
| 2013/0322818 A1* | 12/2013 | Li | G02B 6/262 385/31 |
| 2014/0066756 A1* | 3/2014 | Sinclair | A61B 5/0077 600/427 |
| 2014/0340756 A1* | 11/2014 | Sinclair | A61B 5/0066 359/614 |

OTHER PUBLICATIONS

Xi et al; "High-Resolution OCT Balloon Imaging Catheter With Astimatism Correction"; Opt. Lett. Jul. 1, 2009; 34 (13); 1943-1945.

* cited by examiner

REFLECTIVE OPTICAL COHERENCE TOMOGRAPHY PROBE

This application claims the benefit of priority under 35 U.S.C. § 119 of U.S. Provisional Application Ser. No. 62/101,105 filed on Jan. 8, 2015, the content of which is relied upon and incorporated herein by reference in its entirety.

BACKGROUND

The present disclosure relates to optical coherence tomography, and in particular to a monolithic beam-shaping optical probe for an optical coherence tomography probe.

Optical coherence tomography (OCT) is used to capture a high-resolution cross-sectional image of biological tissues and is based on fiber-optic interferometry. The core of an OCT system is a Michelson interferometer, which typically includes a first optical fiber which is used as a reference arm and a second optical fiber which is used as a sample arm. The sample arm includes the sample to be analyzed, as well as a probe that contains optical components therein. A light source upstream of the probe provides light used in imaging. A photodetector is arranged in the optical path downstream of the sample and reference arms. The probe is used to direct light into or onto the sample and then to collect scattered light from the sample.

Optical interference of light from the sample arm and the reference arm is detected by the photodetector only when the optical path difference between the two arms is within the coherence length of the light from the light source. Depth information from the sample is acquired by axially varying the optical path length of the reference arm and detecting the interference between light from the reference arm and scattered light from the sample arm. A three-dimensional image is obtained by transversely scanning in two dimensions the optical path in the sample arm. The axial/depth resolution of the process is determined by the coherence length, while the overall transverse resolution is dictated by the size of the image spot formed by the optical components of the probe.

Because the probe typically needs to be inserted into a small cavity of the body, it must be small and preferably have a simple optical design. Exemplary designs for the probe include a transparent cylinder in which the miniature probe optical components are contained and through which light is transmitted and received. However, light may be lost due to back reflection when it passes through materials having a different refractive index, thus decreasing image spot intensity. Additionally, back reflections decrease the signal to noise ratio in the data. Moreover, having multiple and separate optical components in the probe is generally problematic because the small optical components have to be assembled and aligned, which adds to the cost and complexity of manufacturing the probe.

SUMMARY

According to one embodiment of the present disclosure, a beam-shaping optical system suitable for use with optical coherence tomography includes a beam-shaping body having a beam-shaping element and an alignment feature. An optical fiber is coupled to the alignment feature. The fiber has a fiber end configured to emit an electromagnetic beam. The fiber and the body are configured to direct the beam into the beam-shaping element such that the beam is shaped into an image spot solely by reflection from the beam-shaping element.

According to another embodiment of this disclosure, an optical coherence tomography probe includes a beam-shaping body integrally defining an alignment feature and a beam-shaping element, the beam-shaping element being an external surface of the beam-shaping body. An optical fiber is coupled to the alignment feature, the fiber having a fiber end configured to emit a beam. The fiber and the body are configured to direct the beam into the beam-shaping element such that the beam is shaped externally of the beam-shaping body.

According to a further embodiment of this disclosure, a method of forming an image spot for optical coherence tomography using an optical fiber includes steps of supporting an optical fiber in an alignment feature of a beam-shaping body having a beam-shaping element, transmitting an electromagnetic beam from the optical fiber into the beam-shaping element, and shaping the beam with the beam-shaping element solely by reflection into the image spot Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

Figure 1:
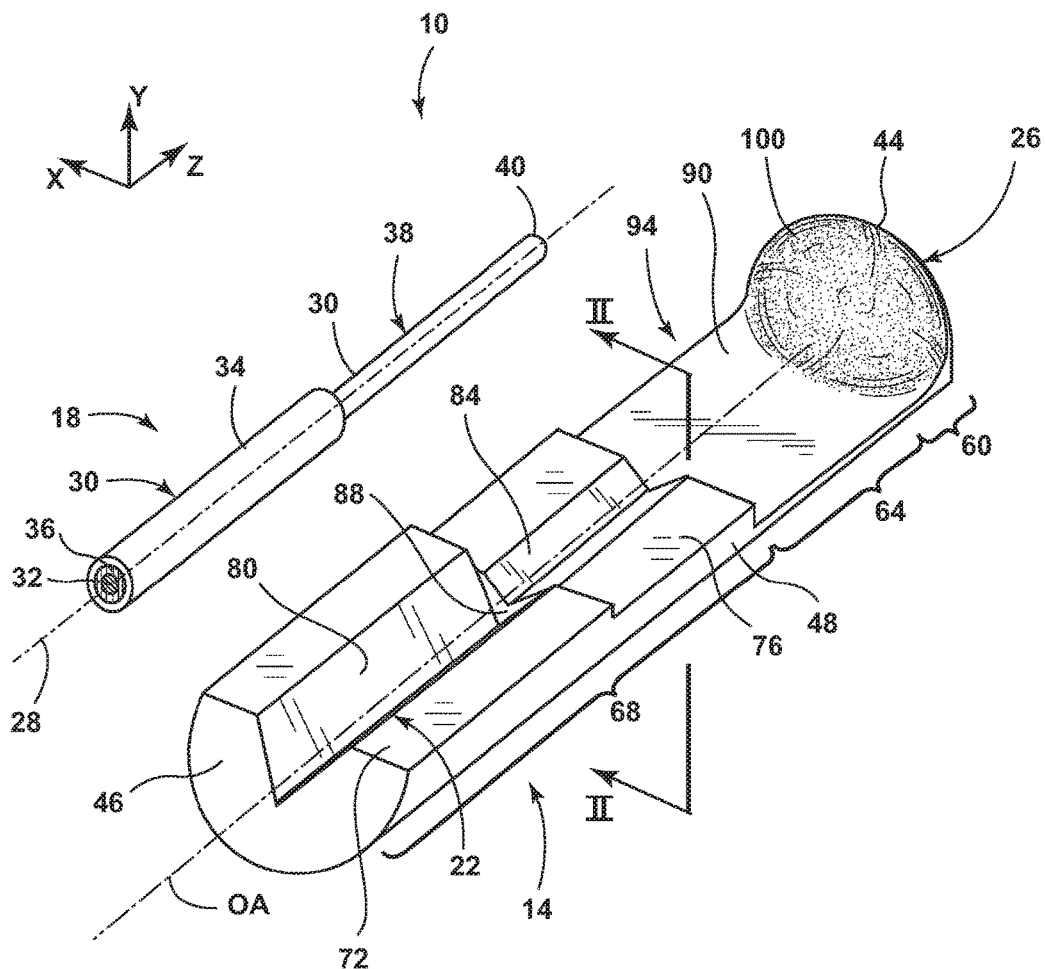
FIG. 1 is an elevated exploded view of an optical probe for use in OCT according to one embodiment.

Reference will now be made in detail to the present preferred embodiments, examples of which are illustrated in the accompanying drawings. Whenever possible, the same reference numerals will be used throughout the drawings to refer to the same or like parts.

For purposes of description herein, the terms "upper," "lower," "right," "left," "rear," "front," "vertical," "horizontal," and derivates thereof shall relate to an optical probe 10 as oriented in FIG. 1, unless stated otherwise. However, it is to be understood that the optical probe 10 may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 2A:
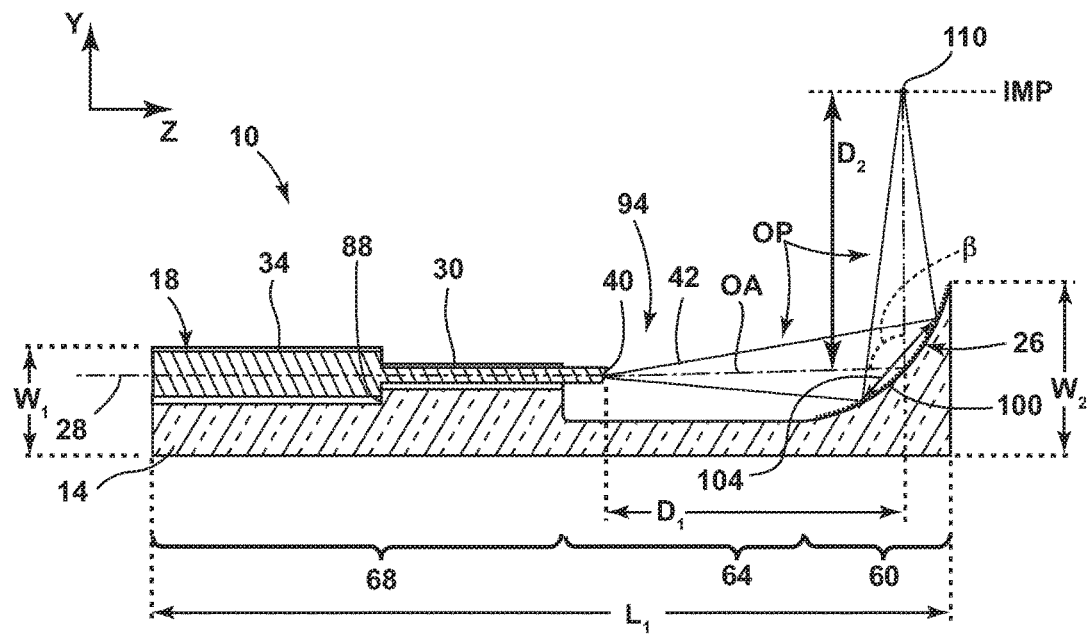
FIG. 2A is a cross-sectional view of the optical probe depicted in FIG. 1 in assembly taken along line II-II according to one embodiment.
Figure 2B:
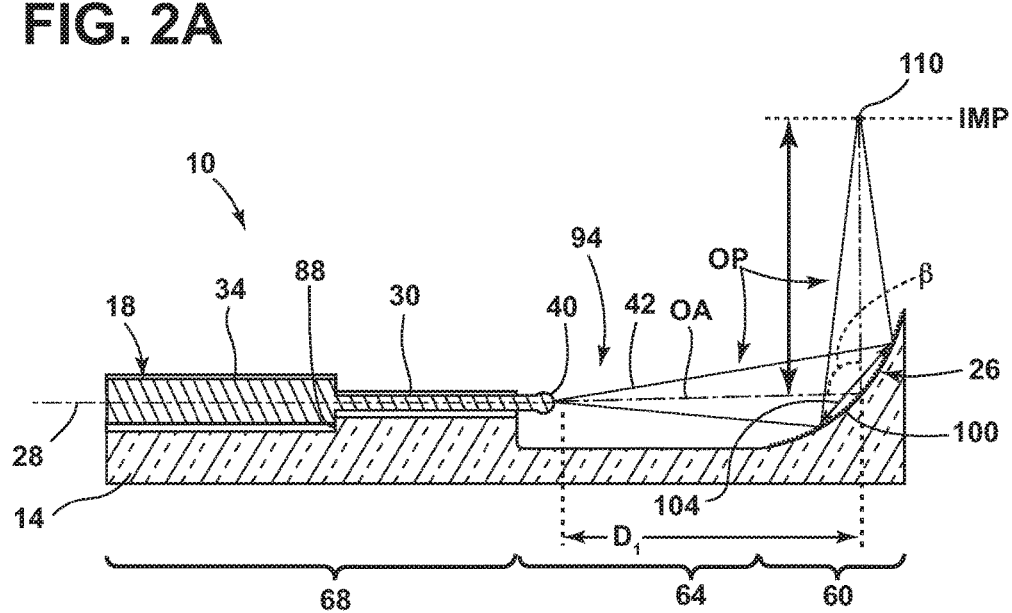
FIG. 2B is a cross-sectional view of the optical probe depicted in FIG. 1 in assembly taken along line II-II according to an alternative embodiment.
Figure 3:
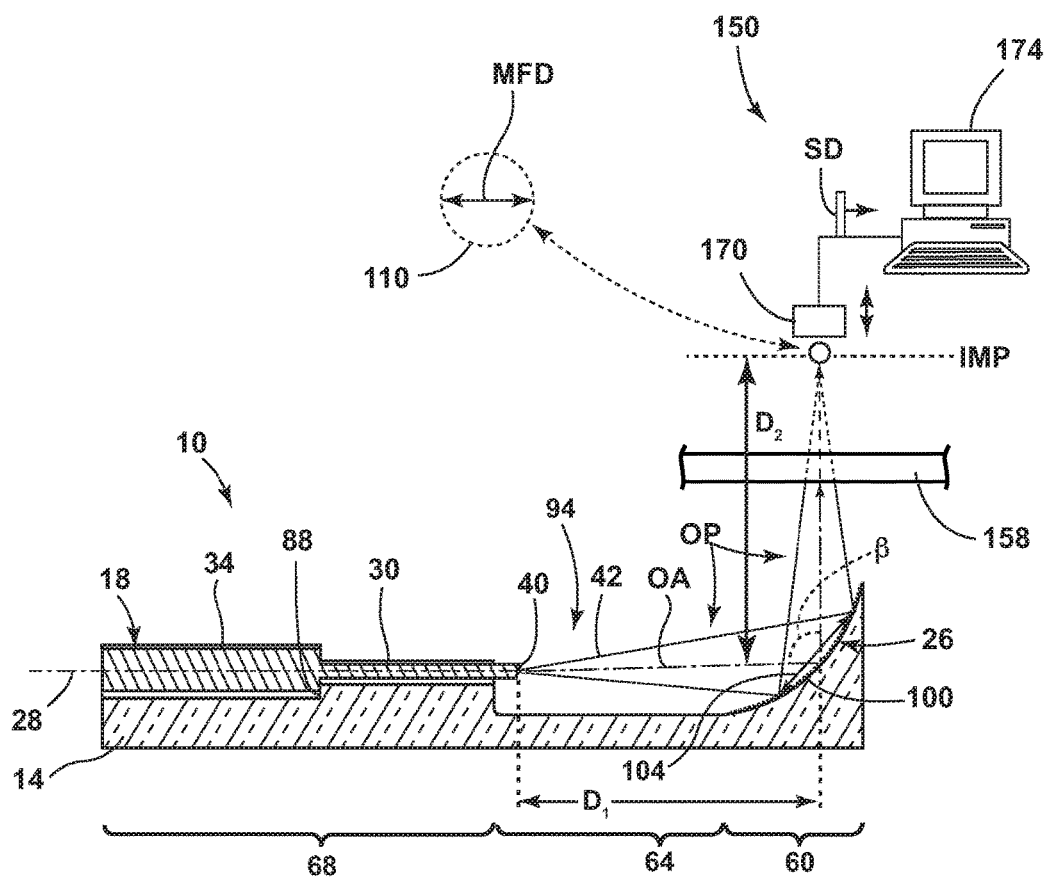
FIG. 3 is a schematic diagram of an OCT alignment system that includes the optical probe according to one embodiment.

Depicted in FIGS. 1-3 is an embodiment of the beam-shaping optical probe 10 suitable for use in OCT and the making of OCT images. The optical probe 10 includes a beam-shaping body 14 to which an optical fiber 18 may be coupled. The beam-shaping body 14 integrally defines an alignment feature 22 and a beam-shaping element 26. The optical fiber 18 has a central axis 28 and includes a cladding 30, a core 32, and a coating 34. In various embodiments the coating 34 is polymeric. In the depicted embodiments, a section of the coating 34 is stripped from the optical fiber 18 to form a coated portion 36 and an uncoated portion 38. The uncoated portion 38 includes a fiber end 40 configured to emit an electromagnetic beam 42. The electromagnetic beam 42 is emitted along an optical axis OA defined by the beam-shaping body 14. In operation, the optical fiber 18 is coupled to the alignment feature 22. In the depicted embodiment, the beam-shaping body 14 is monolithic and integrally defines the beam-shaping element 26 and the alignment feature 22.

Referring now to FIG. 1, in the depicted embodiment, the beam-shaping body 14 includes a front end 44, a back end 46, and an external surface 48. Although the beam-shaping body 14 is monolithic, for convenience, the beam-shaping body 14 can be considered to be three main sections, namely a front section 60 adjacent front end 44 and the beam-shaping element 26, a central section 64 in between the front end 44 and back end 46, and a back section 68 adjacent the back end 46 and the alignment feature 22.

In various embodiments, the beam-shaping body 14 includes a polymeric composition. Exemplary polymeric materials for the beam-shaping body 14 include ZEONOR® (available from Zeon Chemicals L.P., Louisville, Ky.), polyetherimide (PEI), polyethylene, polypropylene, polycarbonate, engineered polymers (e.g., liquid crystal), as well as any other polymeric material or combination of polymeric materials capable of forming the beam-shaping body 14 and producing a smooth surface. In other embodiments, the beam-shaping body 14 may include metals, ceramics, or composites thereof. The beam-shaping body 14 is capable of formation by conventional manufacturing techniques such as injection molding, casting, machining, thermoforming, or extrusion.

In the depicted embodiment the external surface 48 of the back section 68 includes a first flat surface 72 and a second flat surface 76, the alignment feature 22 integrally formed therein. While the beam-shaping body 14 is depicted with the first flat surface 72 elevated relative to the second flat surface 76, various embodiments allow for the flat surfaces 72, 76 to be planar (i.e., no offset). In other embodiments, the second flat surface 76 may be elevated above the first flat surface 72. In the depicted embodiment, the alignment feature 22 includes a first v-shaped groove 80 located in the first flat surface 72 and a second v-shaped groove 84 located in the second flat surface 76. The second v-shaped groove 84 is open to and aligned with the first v-shaped groove 80. It should be understood that the alignment feature 22 may additionally or alternatively incorporate grooves or trenches which are generally circular, square, u-shaped or other shapes operable to couple with the optical fiber 18. In the depicted embodiment, the first and second v-shaped grooves 80, 84 have differing depths and pitches, with the first v-shaped groove 80 having a greater depth and higher pitch than the second v-shaped groove 84.

The differing depths and pitches of the first and second v-shaped grooves 80, 84 allow both the coated and uncoated portions 36, 38 of the optical fiber 18 to be coupled to the beam-shaping body 14 while allowing the central axis 28 of the optical fiber 18 to align substantially coaxial with the optical axis OA of the beam-shaping body 14. Additionally, the differing depths and pitches of the first and second v-shaped grooves 80, 84 serve to define an alignment feature edge 88 between the first and second v-shaped grooves 80, 84 against which the coated portion 36 of the optical fiber 18 butts when optical fiber 18 is coupled in the first and second v-shaped grooves 80, 84. The alignment feature edge 88 assists in properly aligning the optical fiber 18 with the beam-shaping body 14 and also serves to keep the optical fiber 18 in place within the first and second v-shaped grooves 80, 84. Additionally or alternatively, the alignment feature 22 may incorporate a stepped aperture allowing insertion of the optical fiber 18 into the beam-shaping body 14, or other features, for joining the fiber 18 to the back section 68 of the body 14.

In the depicted embodiment, the central section 64 of the beam-shaping body 14 is thinner than the back section 68 and the front section 60. The central section 64 of the exterior surface 48 defines a central surface 90 and an air gap 94. The central surface 90 of the central section 64 extends beneath the optical axis OA of the beam-shaping body 14 between the front section 60 and the back section 68. The air gap 94 allows the fiber end 40 of the optical fiber 18 to extend into the central section 64 above the central surface 90 (FIG. 2A).

Still referring to FIG. 1, the beam-shaping element 26 is integrally defined by the front section 60 of the beam-shaping body 14. The front section 60 of the beam-shaping body 14 extends in an upwardly and inwardly curved manner from the central surface 90 to define the beam-shaping element 26. The beam-shaping element 26 is substantially conic in shape and curves inwardly toward the optical axis OA of the beam-shaping body 14. The conic shape of the beam-shaping element 26 is defined by a radius of curvature along an X-axis and a Y-axis of the beam-shaping body 14.

In order to properly shape the beam 42, the beam-shaping element 26 may have a radius of curvature along the X-axis that is the same or different than a radius of curvature in the Y-axis. The radius of curvature of the X- and Y-axes of the beam-shaping element 26 may have an absolute value of between about 0.5 millimeters and about 10 millimeters, and more specifically, about 1.0 millimeter to about 4.0 millimeters. The conic constant of the X- and Y-axes of the beam-shaping element 26 may independently range from about 1 to about −2, and more specifically between about 0 and about −1. It should be understood that the radii and conic constants of the curvature explained above describe the overall shape of the beam-shaping element 26, and do not necessarily reflect local radii or conic constants of the beam-shaping element 26. The radius of curvature of the X-axis and Y-axis of the beam-shaping element 26 may be adjusted independently in order to correct for any transparent housings or sheaths disposed around the optical probe 10. The conic shape of the beam-shaping element 26 may be decentered along the Y- or Z-axes between about 0.01 millimeters and about 0.8 millimeters. Additionally, the conic shape of the beam-shaping element 26 may have a rotation between the Y- and Z-axes of between about 70° and 120°.

The beam-shaping element 26 is configured to collect and shape (e.g., collimate, converge, and/or change the optical path of) through reflection the electromagnetic beam 42 (FIG. 2A) emitted from the optical fiber 26, as explained in greater detail below. Positioned on the beam-shaping element 26 is a reflective coating 100. Reflective coating 100 may be a dielectric coating, a metal coating, or an enhanced metal coating. Exemplary metal coatings include silver, gold, aluminum, and other lustrous metals capable of reflecting the beam 42. Dielectric materials may include $SiO_2$, $TiO_2$ and combinations thereof. Further, enhanced metal coatings may include a combination of one or more of the previously described metals and/or dielectrics. The reflective coating 100 may also include a capping layer to protect it from environmental conditions (e.g., water, oxygen, and/or sterilization procedures) as well as an adhesion layer to bond the reflective surface 100 to the beam-shaping body 14. The reflective coating 100 is positioned on the beam-shaping element 26 such that the emitted beam 42 is reflected externally to the beam-shaping body 14, and not within it.

Referring now to FIGS. 2A-3, the optical fiber 18 is depicted as protruding from the back section 68 into the air gap 94 above the central surface 90 of the central section 64. In operation, the optical fiber 18 is configured to act as a wave guide for electromagnetic radiation, specifically light at an operating wavelength $\lambda$. The optical fiber 18 carries light from an upstream light source (not shown) to the fiber end 40 where the light is emitted as the electromagnetic beam 42. In one embodiment, the operating wavelength $\lambda$ includes an infrared wavelength such as one in the range from about 850 nanometers to about 1,600 nanometers, with exemplary operating wavelengths $\lambda$ being about 1300 nanometers and about 1560 nanometers.

The optical fiber 18 and the alignment feature 22 of the beam-shaping body 14 are configured to couple such that the electromagnetic beam 42 is emitted from the fiber end 40 on an optical path OP that is both substantially coaxial with the optical axis OA of the beam-shaping body 14, and directed toward the beam-shaping element 26. As the beam 42 is emitted from the fiber end 40, it propagates through the air gap 94 and the diameter of the optical path OP widens with increasing distance from the fiber end 40. A distance $D_1$ between the fiber end 40 and the reflective surface 100 is set based on a desired size of a beam spot 104. The beam spot 104 is the area of light the beam 42 forms as it strikes the beam-shaping element 26. The beam spot 104 grows in diameter with increasing distance from the fiber end 40. In order for the beam-shaping element 26 to properly shape the beam 42, the beam spot 104 must be have the proper diameter when contacting the reflective surface 100 (e.g., approximately half the diameter of the reflective surface 100). Accordingly, the fiber end 40 must be placed a predetermined distance from the beam-shaping element 26 for the beam 42 to be properly shaped. In various embodiments, the distance $D_1$ between the fiber end 40 and the reflective surface 100 may range between about 0.2 millimeters and about 2.6 millimeters. In one embodiment, the distance $D_1$ is about 1.314 millimeters. The diameter of the beam spot 104 may range from about 200 microns to about 800 microns and more specifically, between about 400 microns to about 600 microns.

As the beam 42 enters the beam-shaping element 26, its optical path OP is folded by an angle $\beta$ from reflection off of the reflective coating 100. In the depicted embodiment, the angle $\beta$ is approximately 90°, but in various embodiments can vary by greater than or less than 10° on either side of 90°. The radius of curvature and position of the beam-shaping element 26 determine both the angle $\beta$ that the optical path OP of beam 42 will be folded by, and also a working distance $D_2$ to an image plane IMP where the beam 42 converges to form an image spot 110. Accordingly, the emitted beam 42 is shaped into the image spot 110 solely by reflection from the beam-shaping element 26.

Referring now to FIG. 2A, in various examples the beam-shaping body 14 has an axial length L1 in the range from about 5.0 millimeters to about 10.0 millimeters, back section 68 has a length along the optical axis OA in the range of about 2.0 millimeters to about 5.0 millimeters, and the central section 64 has a length of about 0.2 millimeters to about 2.3 millimeters. Further in the various examples, front section 60 has a length in the range from 0.5 millimeters to 2.0 millimeters. Also, the beam-shaping body 14 has width W1 at back section 68 that can be in the range from 0.3 millimeters to 1.0 millimeters, and has a width W2 at front section 60 that can be in the range from 0.5 millimeters to 2.0 millimeters. The values for these parameters are exemplary and other values and ranges are possible, depending on the particular application.

The fiber end 40 of the optical fiber 18 may be cleaved at an angle in order to prevent undesired back reflection of light into the fiber 18. OCT is particularly sensitive to back reflections of light which have not been scattered off of a sample to be tested (i.e., reflections from the optical probe 10 or refractive surfaces along the optical path OP). The back reflected light may lead to distortion in the OCT image because of increased noise and artifacts. Cleaving the fiber end 40 at an angle minimizes the coupling of the back reflected light back into the optical fiber 18. The fiber end 40 may be cleaved at an angle between about 0° to about 10°, and more particularly between about 6° to 9°. In some embodiments, the alignment feature 22 may be angled with respect to the optical axis OA of the optical probe 10 in order to compensate for the cleaved fiber end 40. The angled alignment feature 22 would keep the optical path OP of the beam 42 substantially coaxial with the optical axis OA of the optical probe 10. Additionally or alternatively, the fiber end 40 may include an anti-reflection film to reduce the amount of reflected light absorbed by the optical fiber 18. The anti-reflection film may include a single or multilayer dielectric material configured to cancel light reflected back to the optical probe 10.

Referring now to FIG. 2B, the fiber end 40 of the optical fiber 18 may also be ball-terminated. According to one embodiment, ball-termination of the optical fiber 18 may be achieved by placing the fiber end 40 between a pair of arc electrodes. The arc electrodes melt the cladding 30 and core 32 of the optical fiber 18. Surface tension of the melted optical fiber 18 forms a substantially spherical ball on the fiber end 40 which then cools and hardens. The electromagnetic beam 42 may be emitted from the ball-termination fiber end 40. The ball-termination of the fiber end 40 may have a diameter of between about 100 microns to about 600 microns, and more specifically between about 200 to about 500 microns.

Similarly to the cleaved fiber end 40 of FIG. 2A, ball-termination of the fiber end 40 of the optical fiber 18 prevents the collection of back reflected light, and thus minimizes distortion of OCT images. Advantageously, ball-termination of the fiber end 40 causes the optical path OP of the emitted beam 42 to diverge faster than the cleaved fiber end 40 as it propagates through the air gap 94 (i.e. the diameter of the beam spot 104 increases faster). Because the optical path OP diverges faster from the ball-terminated fiber end 40, the desired beam spot 104 size may be achieved with a shorter distance $D_1$ between the fiber end 40 and the beam-shaping element 26. This effectively allows the axial length $L_1$ of the optical probe 10 to be shortened compared to embodiments having a cleaved fiber end 40. Similarly to the cleaved fiber end 40 of FIG. 2A, the ball-terminated fiber end 40 of FIG. 2B may include an anti-reflection film.

In an exemplary method for forming an image spot 110 for use in OCT, a first step of supporting an optical fiber 18 in an alignment feature 22 of a beam-shaping body 14 having a beam-shaping element 26 is performed. Next, a step of transmitting an electromagnetic beam 42 from the optical fiber 18 into the beam-shaping element 26 is performed. Finally, a step of shaping the beam 42 with the beam-shaping element 26 solely by reflection into the image spot 110 is performed.

Referring now to FIG. 3, the optical probe 10 is depicted in use within an OCT alignment system 150. As explained above, light traveling within the optical fiber 18 exits the fiber end 40 and is emitted as beam 42 along the optical axis OA. The optical path OP of the beam 42 diverges as it passes through the air gap 94 until it enters the beam-shaping element 26 and reflects from the reflective surface 100. The curvature of the beam-shaping element 26 causes the light to converge uniformly to image point 110 due to the beam-shaping element 26 surface being conic. In the depicted embodiment, as the beam 42 converges, it passes through a portion of a housing 158 which may act as a protective sheath for the optical probe 10. In other embodiments, the optical probe 10 may be used with the optical coherence tomography alignment system 150 without any housing or protective covering. As the beam 42 converges, it forms the image spot 110 at the image plane IMP. The working distance $D_2$ is measured between the horizontal portion of the optical axis OA of the probe and the image plane IMP and may be between about 1 millimeter and about 20 millimeters.

The proper alignment of the optical fiber 18 within beam-shaping body 14 when forming probe 10 is facilitated by the use of the alignment feature 22 and the OCT alignment system 150. In an exemplary method for alignment of the optical fiber 18, a photo detector 170 (e.g., camera or a rotating slit) can be used to capture at least one image of image spot 110 and generate a detector signal SD representative of the captured image. The captured image(s) can be analyzed, e.g., via a computer 174 that is operably connected to photodetector 170. The computer 174 can be used to analyze and display information about the captured image spot(s) 110. In an example, a plurality of image spots 110 are detected and compared to a reference spot (e.g., as obtained via optical modeling based on the design of the optical probe 10) to assess performance.

The mode field diameter MFD is a measure of the spot size or beam width of light propagating in a single mode fiber or at another location in an optical system. The mode field diameter MFD within an optical fiber is a function of the source wavelength, fiber core radius and fiber refractive index profile. In the depicted embodiment, the optical probe 10 is capable of producing an image spot 110 having a mode field diameter MFD of between about 30 microns to about 100 microns at a $1/e^2$ threshold at the image plane IMP. An exemplary mode field diameter of the optical fiber 18 may be 9.2 microns at a $1/e^2$ threshold. The mode field diameter MFD may be sensed as an indicator of the quality of the image spot 110.

The position of optical fiber 18 can be axially adjusted within the alignment feature 22 (e.g., the first and second v-shaped grooves 80, 84) based on making one or more measurements of image spot 110 until an acceptable or optimum image spot 110 is formed. In an example, the one or more measured image spots 110 are compared to a reference image spot or a reference image spot size. The optical fiber 18 can then be fixed in its aligned position within the alignment feature 22. In an example, the coated portion 36 of optical fiber 18 can be fixed (e.g., bonded) within the first v-shaped groove 80 to provide strain relief.

In an exemplary embodiment of optical probe 10, the beam-shaping element 26 has an X-axis radius of curvature of about 1.16 millimeters corresponding to a conic constant of about 0.5858 and a Y-axis radius of curvature of about 1.2935 millimeters corresponding to a conic constant of about 0.8235. Further, the conic shape of the beam-shaping element 26 is decentered along the Y-axis by about 0.7 millimeters, decentered along the Z-axis by about 0.089 millimeters, and has a rotation between the Y- and Z-axes of about 89.7°. The distance $D_1$ between the fiber end 40 and reflective surface 100 is about 1.314 millimeters. Such an optical probe is capable of forming the image spot 110 at a working distance $D_2$ of about 9.0 millimeters with a mode field diameter MFD of about 64 microns at the $1/e^2$ threshold.

Because optical probe 10 and the exemplary optical coherence tomography alignment system 150 has a monolithic beam-shaping body 14 which defines a reflective beam-shaping element 26, the system has no need for the use of spacers, GRIN lenses or refractive elements such as lenses. Further, eliminating the use of multiple optical components is beneficial because there are fewer material interfaces which may result in optical back reflections or vignetting of the image spot 110. Additionally, by shaping the beam 42 into the image spot 110 solely based on reflection, higher power light sources may be used than conventional optical probes. Optical probes utilizing polymers as a refractive element are limited in the intensity of light they may refract; however, reflective systems do not have such limitations.

Moreover, because the optical probe 10 uses a single reflective beam-shaping element 26 defined by the monolithic beam-shaping body 14, in contrast to a multi-component system, differences in the coefficient of thermal expansion between different components do not exist. For example, in prior art designs, lenses and reflective surfaces may come out of alignment due to a temperature differential between the operating temperature and the temperature at which the probe was calibrated and/or assembled. In the monolithic, single reflective surface design of the present disclosure, this is less likely to happen due to all components having the same coefficient of thermal expansion because all components are composed of the same material. Additionally, due to the simplistic design of the present disclosure, the manufacturing of the optical probe 10 is simplified and therefore less expensive to make.

Figure 4:
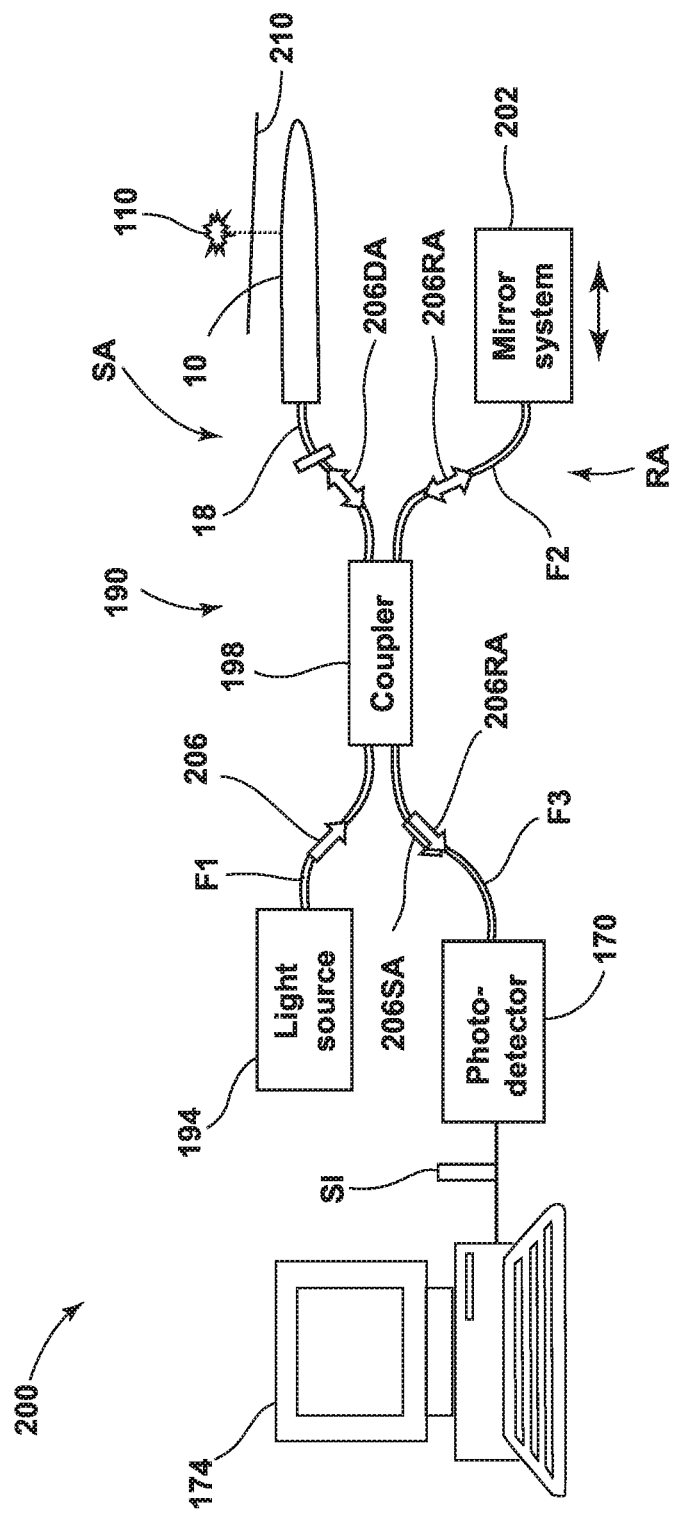
FIG. 4 is a schematic diagram of an OCT system that includes an optical probe according to one embodiment.

FIG. 4 illustrates an exemplary OCT system 200 that includes an embodiment of the optical probe 10 as disclosed herein. OCT system 200 includes a light source 194 and an interferometer 190. The light source 194 is optically connected to a fiber optic coupler ("coupler") 198 via a first optical fiber section FI. OCT probe 10 is optically connected to coupler 198 via optical fiber 18 and constitutes the sample arm SA of the interferometer 190. OCT system 200 also includes a movable mirror system 202 optically connected to coupler 198 via an optical fiber section F2. Mirror system 202 and optical fiber section F2 constitute a reference arm RA of the interferometer 190. Mirror system 202 is configured to alter the length of the reference arm, e.g., via a movable mirror (not shown). OCT system 200 further includes the photodetector 170 optically coupled to coupler 198 via a third optical fiber section F3. Photodetector 170 in turn is electrically connected to computer 174.

In operation, light source 194 generates light 206 that travels to interferometer 190 over optical fiber section FI. The light 206 is divided by coupler 198 into light 206RA that travels in reference arm RA and light 206SA that travels in sample arm SA. The light 206RA that travels in reference arm RA is reflected by mirror system 202 and returns to coupler 198, which directs the light to photo detector 170. The light 206SA that travels in sample arm SA is processed by optical probe 10 as described above (where this light was referred to as just emitted beam 42) to form image spot 162 on or in a sample 210. The resulting scattered light is collected by optical probe 10 and directed through optical fiber 18 to coupler 198, which directs it (as light 206SA) to photo detector 170. The reference arm light 206RA and sample arm light 206SA interfere and the interfered light is detected by photodetector 170. Photodetector 170 generates an electrical signal SI in response thereto, which is then sent to computer 174 for processing using standard OCT signal processing techniques.

The optical interference of light 206SA from sample arm SA and light 206RA from reference arm RA is detected by photodetector 170 only when the optical path difference between the two arms is within the coherence length of light 206 from light source 194. Depth information from sample 210 is acquired by axially varying the optical path length of reference arm RA via mirror system 202 and detecting the interference between light from the reference arm and scattered light from the sample arm that originates from within the sample. A three-dimensional image is obtained by transversely scanning in two dimensions the optical path in the sample arm SA. The axial resolution of the process is determined by the coherence length.

It should be understood that although the use of the optical probe 10 was described in connection with only one OCT technique, the optical probe 10 may be used in a wide variety of applications, including other OCT techniques (e.g., Frequency Domain OCT, Spectral Domain OCT).

While the embodiments disclosed herein have been set forth for the purpose of illustration, the foregoing description should not be deemed to be a limitation on the scope of the disclosure or the appended claims. It will be apparent to those skilled in the art that various modifications and variations can be made without departing from the spirit or scope of the claims.

It will be understood by one having ordinary skill in the art that construction of the described invention and other components is not limited to any specific material. Other exemplary embodiments of the invention disclosed herein may be formed from a wide variety of materials, unless described otherwise herein. In this specification and the amended claims, the singular forms "a," "an," and "the" include plural reference unless the context clearly dictates otherwise.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It will be apparent to those skilled in the art that various modifications and variations can be made without departing from the spirit or scope of the claims.

What is claimed is:

1. A beam-shaping optical system suitable for use with optical coherence tomography, comprising:
    a beam-shaping body comprising a reflective beam-shaping element with optical power and an optical fiber alignment feature, wherein an air gap is defined between the reflective beam-shaping element and optical fiber alignment feature; and
    an optical fiber coupled to the alignment feature such that only the air gap extends between the fiber and the reflective beam-shaping element, the fiber having a fiber end configured to emit an electromagnetic beam and the fiber end is ball-terminated;
    wherein the fiber and the body are configured to direct the beam into the beam-shaping element such that the beam leaving the end face of the optical fiber is shaped into an image spot solely by reflection from the beam-shaping element, further wherein the fiber extends into the air gap.

2. The beam-shaping optical system of claim 1, wherein the reflective beam-shaping element has a concave surface facing the fiber end.

3. A beam-shaping optical system suitable for use with optical coherence tomography, comprising:
    a beam-shaping body comprising a reflective beam-shaping element separated from an alignment feature by an air gap; and
        an optical fiber coupled to the alignment feature such that a fiber end of the fiber extends into the air gap and is configured to emit an electromagnetic beam, wherein the fiber end of the optical fiber is ball-terminated, wherein the fiber with the ball-terminated fiber end and the body are configured to direct the beam into the beam-shaping element such that the beam leaving the ball-terminated end face of the optical fiber is shaped into an image spot only by reflection from the beam-shaping element.

4. The beam-shaping optical system of claim 3, wherein the beam-shaping element is defined from a curved surface of the beam-shaping body and comprises a dielectric, metal, or enhanced metal coating.

5. The beam-shaping optical system of claim 4, wherein the beam-shaping element has a radius of curvature between about 1.0 millimeters and about 4.0 millimeters.

6. The beam-shaping optical system of claim 3, wherein the electromagnetic beam has a wavelength between about 850 nanometers and about 1600 nanometers.

7. The beam-shaping optical system of claim 3, wherein the beam-shaping body defines the beam-shaping element and alignment feature as a monolithic body.

8. The beam-shaping optical system of claim 3, wherein the alignment feature includes a v-shaped groove.

9. An optical coherence tomography probe, comprising:
a beam-shaping body integrally defining an alignment feature and a beam-shaping element, the beam-shaping element being an external surface of the beam-shaping body; and
an optical fiber coupled to the alignment feature, the fiber having a fiber end configured to emit a beam and wherein the fiber end of the optical fiber extends into an air gap and is ball-terminated,
wherein the fiber and the body are configured to direct the beam into the beam-shaping element such that the beam is shaped by the a beam-shaping element externally of the beam-shaping body.

10. The optical coherence tomography probe of claim 9, wherein the beam-shaping element has a radius of curvature between about 1.0 millimeters and about 4.0 millimeters.

11. The optical coherence tomography probe of claim 9, wherein the beam-shaping element is a curved surface of the beam-shaping body and comprises a dielectric, metal, or enhanced metal coating.

12. The optical coherence tomography probe of claim 9, wherein the electromagnetic beam has a wavelength between about 850 nanometers and about 1600 nanometers.

13. The optical coherence tomography probe of claim 12, wherein the alignment feature includes a v-shaped groove.

14. A method of forming an image spot for optical coherence tomography using an optical fiber, comprising the steps:
supporting an optical fiber in an alignment feature of a beam-shaping body having a beam-shaping element such that a fiber end of the fiber extends into an air gap and is ball-terminated;
transmitting an electromagnetic beam entirely within the air gap from the optical fiber to the external surface of the beam-shaping element; and
shaping the beam with the beam-shaping element by reflection into the image spot.

15. The method of claim 14, wherein the alignment feature and the beam-shaping element are integrally defined by the beam-shaping body.

16. The method of claim 15, wherein the beam-shaping element has a radius of curvature between about 1.0 millimeters and about 4.0 millimeters.

17. The method of claim 16, wherein the electromagnetic beam has a wavelength between about 850 nanometers and about 1600 nanometers.

* * * * *